| United States Patent [19] | [11] Patent Number: 5,034,328 |
|---|---|
| Boyette | [45] Date of Patent: Jul. 23, 1991 |

[54] CONTROL OF HEMP SESBANIA WITH A FUNGAL PATHOGEN *COLLETOTRICHUM TRUNCATUM*

[75] Inventor: Clyde D. Boyette, Leland, Miss.

[73] Assignee: The United States of America as represented by the Secretary of Agriculture, Washington, D.C.

[21] Appl. No.: 338,680

[22] Filed: Apr. 17, 1989

[51] Int. Cl.$^5$ .............................................. C12N 1/14
[52] U.S. Cl. ..................................... 435/254; 435/911
[58] Field of Search .................................. 435/254, 911

[56] References Cited

U.S. PATENT DOCUMENTS 4,715,881 12/1987 Andersen et al. ...................... 71/79

OTHER PUBLICATIONS

Boyette, C. D., "Efficacy and Host Range of a Recently Discovered Funga Pathogen for Biocontrol of Hemp Sesbania", Meeting on Environmental Legislators and Its Effects on Weed Science.

Klerk et al., "Interaction of Pesticides . . . Rice", 35th Annual Meeting of the Southern Weed Science Society on New Perspectives in Weed Science, Jan. 19–21, 1982, Atlanta, Ga.

*Primary Examiner*—Douglas W. Robinson
*Assistant Examiner*—Marian C. Knode
*Attorney, Agent, or Firm*—M. Howard Silverstein; John D. Fado; Curtis P. Ribando

[57] ABSTRACT

A strain of *Colletotrichum trancatum* has been discovered which is selectively pathogenic toward hemp sesbania (*Sesbania exaltata*). Formulations incorporating propagules of the fungal pathogen are useful for biological control of the hemp sesbania weed, particularly in agriculatural fields.

1 Claim, No Drawings

CONTROL OF HEMP SESBANIA WITH A FUNGAL PATHOGEN *COLLETOTRICHUM TRUNCATUM*

BACKGROUND OF THE INVENTION

1. Field of the Invention

This invention relates to a method of controlling hemp sesbania by infection with a fungal pathogen, *Colletotrichum truncatum*.

2. Description of the Prior Art

Hemp sesbania (*Sesbania exaltata*) is an economically troublesome weed in soybean production on aluvial clay soils of the lower Mississippi River Valley [McWhorter et al., *Weed Science*, Vol. 27 (1979), pp. 58-63]. It can cause crop yield reductions by competing for nutrients and water, and by shading the crop plants. It can also reduce crop quality by increasing the amount of foreign material and moisture in harvested beans and by increasing the number of damaged kernels. This weed is also a threat in cotton and rice production.

The procedures for using pathogens to control weeds in annual crops have been described previously for various fungal species. Daniel et al., U.S. Pat. No. 3,849,104, teaches the use of an endemic anthracnose fungus, *Colletotrichum gloeosporioides* forma specialis *aeschynomene*, to control the northern jointvetch weed in rice fields. A related species, *C. malvarum*, has been reported by Templeton in U.S. Pat. No. 3,999,973 as a control for prickly sida (*Sida spinosa* L.) or teaweed, particularly in soybean and cotton fields. *C. malvarum* is also pathogenic toward other noncultivated species, including velvetleaf. *C. coccodes* has been well documented as a widely distributed pathogen of potato and tomato, as well as 35 other plant species throughout the world. One isolate of *C. coccodes* has been studied as a potential mycoherbicide for velvetleaf by Gotlief et al. [*Proceedings, Weed Science Society of America*, Vol. 37 (1984), p. 68]. Anderson et al., U.S. Pat. No. 4,715,881, disclose the use of a strain of *C. coccodes* as a selective pathogen toward eastern black nightshade.

Walker [*Weed Science*, Vol. 29 (1981), pp. 505-507] discloses the use of *Alternaria macrospora* as a pathogen against spurred anoda. In Walker, U.S. Pat. No. 4,390,360, *A. cassiae* is disclosed as an effective biological control agent for sicklepod, showy crotalaria, and coffee senna. Finally, Walker teaches in U.S. Pat. No. 4,419,120 that *Fusarium lateritium* is useful in controlling prickly sida, velvetleaf, and spurred anoda.

SUMMARY OF THE INVENTION

I have now discovered a strain of *Colletotrichum truncatum* that is selectively pathogenic toward hemp sesbania, a weed that is not affected or controlled by any other known biological herbicide. Furthermore, this strain of *C. truncatum* is innocuous toward virtually all crop species for which the hemp sesbania poses agronomic difficulties. This invention is drawn to the use of this fungus as a mycoherbicide for controlling hemp sesbania and other susceptible species, and also to mycoherbicidal compositions comprising *C. truncatum* propagules. In practice, the target plants are inoculated by treating infested fields with the propagule-containing compositions.

In accordance with this discovery, it is an object of this invention to provide a mycoherbicidal alternative to chemical control of hemp sesbania.

It is also an object of the invention to provide a biological herbicide for hemp sesbania which is nonpathogenic toward crop species.

Another object of the invention is to provide a fungal pathogen which can be artificially mass-produced and formulated for both preemergence and postemergence weed control.

Other objects and advantages of this invention will become readily apparent from the ensuing description.

DETAILED DESCRIPTION OF THE INVENTION

The fungal organism for use herein is a strain of *C. truncatum* isolated from hemp sesbania seedlings in the Southern Weed Science Laboratory, Stoneville, Miss. This strain was found to be responsible for a previously unknown anthracnose disease that kills infected plants as a result of stem-girdling lesions.

The taxonomic characteristics of this isolate are characteristic of the species. The acervuli are dark, oval to elongate, hemispheric to truncate-conical, and erumpent with numerous setae. Conidia are hyaline, aseptate, truncate in shape, measuring 18-25 by 3-5 $\mu$m, and are borne singly on the conidiophores. Setose sclerotia are common. This isolate has been deposited under the conditions of the Budapest Treaty in the Agricultural Research Service Culture Collection (NRRL) in Peoria, Ill., and has been assigned the Accession No. NRRL 18434.

The fungal propagules, including the spores (conidia) and mycelia, can be mass-produced for field inoculations by any conventional means. For example, abundant conidia are produced by culturing the *C. truncatum* on potato dextrose agar, and highly infectious sclerotia are produced in shake culture on soyflour-cornmeal medium or modified Richard's V-8 medium.

The propagules are preferably incorporated into compositions suitable for field application. They can be combined with any liquid vehicle or solid carrier such as water, emulsions, sodium alginate, clay, vermiculite, $CaCO_3$, corn cob grits, etc. Both the spores and the mycelia lend themselves to formulation as liquid sprays and wettable powders for postemergence treatment. They can also be formulated as controlled-release granules for preemergence weed control. The pathogen will infect and kill hemp sesbania plants within a temperature range of 10°-40° C.; the optimum range is 20°-35° C. A period of free moisture (dew) is required for optimal pathogenesis and mortality to occur; the optimum is 4 hr or more. The pathogen infects and kills weeds over a broad range of sizes and growth stages. The pathogen is most effective as a biological herbicide when applied to plants that are in the cotyledonary to fifth leaf stage of growth.

The actual concentration of propagules in the formulated composition is not particularly critical, and is a function of practical considerations such as the properties of the vehicle or carrier, and the method of application. For purposes of formulation and application, an "effective amount" is defined to mean any such quantity of propagules sufficient to infect the target plant and thereby induce the symptoms of the disease described below.

It is understood that application of the mycoherbicide does not require immediate direct contact with the target plant. It may be applied in the locus or vicinity of the plant, and relies upon natural environmental conditions for infection. In this manner, the herbicide is effective as a preemergent treatment.

Though current data indicate that NRRL 18434 is an extremely selective pathogen of hemp sesbania, it is within the compass of this invention to treat other undesirable plant species which prove to be susceptible to this disease. When infecting hemp sesbania, the organism produces orbicular lesions with dark, concentric circles, 2-4 mm in diameter. Microscopic examinations revealed pustules of truncate conidia, 18-25 by 3-5 micron, surrounded by dark setae. NRRL 18434 is innocuous toward several cultivars of soybean, cotton, rice, garden bean, and tomato, as well as 19 other plant species representing a total of 7 families. Three cultivars of the soybeans tested sustained very slight injury, but they outgrew the injury after 3 weeks.

The following examples are intended only to further illustrate the invention and are not intended to limit the scope of the invention which is defined by the claims.

EXAMPLE 1

Pathogen Isolation and Culture

*Colletotrichum truncatum* was isolated from a diseased seedling of hemp sesbania on potato-dextrose agar (PDA-A) amended with the antibiotics chloramphenicol (0.75 mg/ml) and streptomycin sulfate (1.25 mg/ml). After 48 hr at 25° C., advancing edges of fungal colonies were transferred to PDA-A, and incubated for 5 days at 25° C. under alternating 12-hr periods of light and darkness. Light was provided by four, 40-watt cool fluorescent lamps. Advancing edges of the colonies containing mycelium and spores were subcultured on PDA without antibiotics and preserved in screw-capped culture tubes of twice-autoclaved sandy loam soil, then stored at 4° C. Inoculum was increased on petri plates of PDA amended with 1.5 g/L L-proline (PDA-P) by flooding them with 1-ml suspensions of spores from the subculture plates. The plates were incubated for 3-5 days under the same temperature and lighting conditions as previously described. Conidia were washed from the plates using sterile distilled water containing Sterox NJ surfactant nonoxynol (9-10 POE) [α-(p-nonylphenyl)-ω-hydroxy(oxyethylene)].

EXAMPLE 2

Hemp sesbania plants were grown in a commercial potting mix on peat strips that contained 12 plants each. The potting mix was supplemented with a slow-release, 14:14:14 fertilizer. The plants were placed on subirrigated benches in the greenhouse at temperatures ranging from 25°-30° C. with 40-90% relative humidity. The photoperiod was 12 hr with 1650 micromol m$^{-2}$ sec$^{-1}$ photosynthetically active radiation (PAR) as measured at midday. At the cotyledonary to fifth-true-leaf stage of growth, the plants were inoculated by spraying until runoff with conidial preparations containing $2 \times 10^6$ conidia per ml and 0.02% surfactant. Control plants were sprayed with water containing only surfactant. Immediately after inoculation the plants were placed in a darkened dew chamber for 12 hr at 25° C., then transferred to subirrigated greenhouse benches. The plants were monitored for disease development for 3 weeks. NRRL 18434 was highly virulent on hemp sesbania at all stages of growth that were tested. Cotyledonary plants were killed within 3 days as a result of necrosis occurring on all tissues. Larger plants were killed within 5-7 days, but anthracnose lesions occurred only on stems and petioles.

EXAMPLE 3

To determine the host range of *C. truncatum*, the procedure of Example 2 was repeated with the test plants listed in Table I, except that plants were inoculated at the cotyledonary to third-true-leaf stage of growth. Each species or cultivar was inoculated on two separate dates, with 36 plants used for each treatment.

*S. exaltata* was the only test plant that was killed (Table I). A related species, *S. drummondii* was not affected by the fungus, nor were most of the other plants that were inoculated. Some limited infection occurred on 'Bragg', 'Bedford', and 'Hill' cv. soybeans, but it was restricted to small (<3 mm) leaf spots. The fungus was recovered from the lesions, but it did not sporulate on the necrotic soybean tissue, and all of the infected soybean plants had recovered from the infection after 3 weeks. Soybeans were re-inoculated with *C. truncatum* isolated from soybeans, but no increased virulence on soybeans by the pathogen occurred.

EXAMPLE 4

To study the effect of dew period duration, the procedure of Example 2 was repeated except that greenhouse temperatures were maintained between 28°-32° C. with 40-60% relative humidity (RH) and the hemp sesbania plants were inoculated at the second-to-fourth leaf stage of growth with a spray concentration of $2 \times 10^7$ spores/ml. The plants were in the darkened dew chamber for periods of 0, 2, 4, 6, 8, 12, 16, or 24 hr, and then returned to the greenhouse for 14 days.

TABLE I

| FAMILY<br>Common Name, Scientific Name, Cultivar | Disease<br>Reaction[a] |
|---|---|
| COMPOSITAE | |
| Cocklebur (*Xanthium pennsylvanicum* Wallr.) | R |
| CONVOLVULACEAE | |
| Morningglory (*Ipomoea* spp.) | R |
| CUCURBITACEAE | |
| Pumpkin (*Cucurbita pepo* L.)<br>'Jack-O'Lantern' | R |
| Squash (*Cucurbita pepo* var. *melopepo* (L.) Alef.)<br>'Golden Summer Crookneck' | R |
| Watermelon (*Citrullus vulgaris* Schrl.)<br>'Charleston Grey' | R |
| GRAMINAE | |
| Corn (*Zea mays* L.)<br>'Truckers Favorite' | R |
| Johnsongrass (*Sorghum halepense* (L.) Pers.) | R |
| Rice (*Oryza, sativa* L.) | |
| 'LaBelle' | R |
| 'Starbonnet' | R |
| Grain sorghum (*Sorghum bicolor* (L.) Moench)<br>'Texas C-124' | R |
| LEGUMINOSAE | |
| Alfalfa (*Medicago sativa* L.)<br>'Delta' | R |
| Coffee senna (*Cassia occidentalis* L.) | R |
| Sicklepod (*Cassia obtusifolia* L.) | R |
| Florida beggarweed (*Desmodium tortuosum* L.) | R* |
| Showy crotalaria (*Crotalaria spectabilis* L.) | R |
| Hemp sesbania (*Sesbania exaltata* (Raf.) Cory.) | HS |
| Rattlebox (*Sesbania drummondii* L.) | R |
| Northern jointvetch (*Aeschynomene virginica*<br>(L.) B.S.P.) | R* |
| Soybean (*Glycine max* (L.) Merr.) | |
| 'Bedford' | SS |
| 'Bragg' | SS |
| 'Dare' | R |
| 'Davis' | R |
| 'Forrest' | R |

TABLE I-continued

| FAMILY<br>Common Name, Scientific Name, Cultivar | Disease Reaction[a] |
|---|---|
| 'Hill' | R* |
| 'Hood' | R |
| 'Centennial' | R |
| 'Tracy' | R |
| Peanut (*Arachis hypogoea* L.) | R |
| 'Tennessee Reds' | |
| Garden bean (*Phaseolus vulgaris* L.) | |
| 'Kentucky Wonder' | R |
| 'Romano Pole' | R |
| 'Ohio Pole' | R |
| 'Jackson Wonder' | R |
| 'Henderson Bush Lima' | R |
| 'Lady Cowpea' | R |
| 'White Crowder Pea' | R |
| MALVACEAE | |
| Cotton (*Gossypium hirsutum* L.) | |
| 'Stoneville 213' | R |
| 'Deltapine 61' | R |
| Prickly sida (*Sida spinosa* L.) | R |
| Velvetleaf (*Abutilon theophrasti* Medic.) | R |
| SOLANACEAE | |
| Tomato (*Lycopersicon esculentum* Mill) | |
| 'Beefsteak' | R |
| 'Marion' | R |
| Jimsonweed (*Datura stramonium* L.) | R |

[a]R = Resistant; no disease symptoms
R* = Resistant; 'flecking'; plants outgrew symptoms
SS = Slightly Susceptible; small (<2 mm) lesions-fungus recovered; plants outgrew symptoms
HS = Highly Susceptible; severe necrosis, lesion coalescence; all or most plants killed With only 4 hr of dew, 84% mortality occurred; and after 6 hr, 100% of the plants were killed. Even in the absence of dew, 17% mortality occurred.

EXAMPLE 5

The procedure of Example 4 was repeated except that the plants were inoculated at the growth stages and at the spore concentrations listed in Table II. The dew duration was 8 hr. The results are reported in Table II, below.

EXAMPLE 6

The procedure of Example 4 was repeated except that the plants were in the dew chamber for 8 hr with dew temperatures of either 15°, 20°, 25°, or 30° C. The plants were then placed in environmental chambers for 2 weeks where photoperiods were 12 hr with 875 micromol $m^{-2} sec^{-1}$ PAR at 75-90% RH and day/night temperatures were either 20/10, 25/15, 30/20, or 35/25, respectively. The results are reported in Table III, below.

It is understood that the foregoing detailed description is given merely by way of illustration and that modification and variations may be made therein without departing from the spirit and scope of the invention.

TABLE II

| Plant Growth Stage | Inoculum Concentration (spores/ml) | | | | | | Correlation (r-values)[b] |
|---|---|---|---|---|---|---|---|
| | 0 | $10^3$ | $10^4$ | $10^5$ | $10^6$ | $10^7$ | |
| | % Mortality[a] | | | | | | |
| Cotyledon-to-first leaf | 0 | 42a | 100a | 100a | 100a | 100a | 0.504 |
| 2 to 4 leaves | 0 | 22b | 94a | 97a | 100a | 100a | 0.533 |
| 5 to 7 leaves | 0 | 17b | 56b | 66b | 78b | 100a | 0.792* |
| 7 to 10 leaves | 0 | 0c | 17c | 34c | 67c | 72b | 0.792* |

[a]Values in each column followed by the same letter are not significantly different at the 5% level, according to Duncan's multiple range test.
[b]Correlation of values within rows * significant at the 80% level.

TABLE III

| Temperature Regime (Day/Night/Dew) | Mortality, %[a] |
|---|---|
| 20/10/15 | 100a |
| 25/15/20 | 100a |
| 30/20/25 | 84b |
| 35/25/30 | 37c |

[a]Values followed by the same letter are not significantly different at the 5% level, according to Duncan's multiple range test.

I claim:
1. A biologically pure culture of *Colletotrichum truncatum* having all the identifying characteristics of *Colletotrichum truncatum* NRRL 18434.

* * * * *